(12) United States Patent
Carucci et al.

(10) Patent No.: US 9,314,435 B2
(45) Date of Patent: Apr. 19, 2016

(54) STABLE FORMULATIONS OF ANTIPLATELET AGENTS, OMEGA-3 FATTY ACIDS AND AMYLOSE IN SOFT GELATIN CAPSULES

(71) Applicant: ALTERGON S.A., Lugano (CH)

(72) Inventors: Simone Carucci, Lugano (CH); Alberto Bernareggi, Lugano (CH); Maurizio Marchiorri, Lugano (CH); Marco Pontiggia, Lugano (CH)

(73) Assignee: ALTERGON S.A., Lugano (CH)

( * ) Notice: Subject to any disclaimer, the term of this patent is extended or adjusted under 35 U.S.C. 154(b) by 0 days.

(21) Appl. No.: 14/362,161

(22) PCT Filed: Dec. 4, 2012

(86) PCT No.: PCT/EP2012/074354
§ 371 (c)(1),
(2) Date: Jun. 2, 2014

(87) PCT Pub. No.: WO2013/083558
PCT Pub. Date: Jun. 13, 2013

(65) Prior Publication Data
US 2014/0335171 A1  Nov. 13, 2014

(30) Foreign Application Priority Data
Dec. 5, 2011  (IT) .............................. MI2011A2221

(51) Int. Cl.
| | | |
|---|---|---|
| *A61K 9/48* | (2006.01) | |
| *A61K 31/60* | (2006.01) | |
| *A61K 31/202* | (2006.01) | |
| *A61K 31/616* | (2006.01) | |
| *A61K 31/232* | (2006.01) | |

(52) U.S. Cl.
CPC .............. *A61K 9/4866* (2013.01); *A61K 9/4808* (2013.01); *A61K 9/4816* (2013.01); *A61K 9/4825* (2013.01); *A61K 9/4858* (2013.01); *A61K 31/202* (2013.01); *A61K 31/232* (2013.01); *A61K 31/616* (2013.01)

(58) Field of Classification Search
CPC . A61K 9/4808; A61K 9/4816; A61K 9/4858; A61K 9/4866; A61K 31/606; A61K 31/202
See application file for complete search history.

(56) References Cited

U.S. PATENT DOCUMENTS

| | | | | |
|---|---|---|---|---|
| 3,456,051 | A * | 7/1969 | Hiroyuki et al. .............. | 424/455 |
| 5,554,385 | A * | 9/1996 | Stroud .......................... | 424/456 |
| 2003/0199481 | A1* | 10/2003 | Garavani et al. ............. | 514/165 |
| 2009/0192126 | A1* | 7/2009 | Casey et al. .................. | 514/163 |
| 2010/0178335 | A1* | 7/2010 | Echanagorria et al. ....... | 424/452 |

FOREIGN PATENT DOCUMENTS

| | | |
|---|---|---|
| WO | WO92/09274 | 6/1992 |
| WO | WO2008/025819 | 3/2008 |
| WO | WO2008/068276 | 6/2008 |
| WO | WO2011/060944 | 5/2011 |

OTHER PUBLICATIONS

International Search Report and Written Opinion of PCT/EP2012/074354.

* cited by examiner

*Primary Examiner* — Lakshmi Channavajjala
(74) *Attorney, Agent, or Firm* — Silvia Salvadori, P.C.; Silvia Salvadori

(57) ABSTRACT

The invention discloses stable formulations of acetylsalicylic acid or salts thereof, omega-3 fatty acids and amylose in soft gelatin capsules.

9 Claims, No Drawings

STABLE FORMULATIONS OF ANTIPLATELET AGENTS, OMEGA-3 FATTY ACIDS AND AMYLOSE IN SOFT GELATIN CAPSULES

This application is a U.S. National stage of PCT/EP2012/074354 filed on Dec. 4, 2012, which claims priority to and the benefit of Italian application serial No.: MI2011A0022221 filed on Dec. 5, 2011, the contents of which are incorporated herein by reference in their entirety.

The present invention relates to stable formulations of acetylsalicylic acid or salts thereof, omega-3 fatty acids and amylose in soft gelatin capsules.

INTRODUCTION

Acetylsalicylic acid (ASA) is a well-known non-steroidal anti-inflammatory drug (NSAID) belonging to the salicylate family. At low or moderate doses of 50-325 mg/day, ASA is used as an antiplatelet agent for the prevention and treatment of strokes, coronary disease and heart attacks. According to the results of the Physicians' Health Study-I (1), low doses of ASA (325 mg on alternate days) reduce the risk of the first heart attack by 44%.

Omega-3 fatty acids (or PUFA n-3) are a category of essential fatty acids which are indispensable for the body to function correctly. Above all, they are essential to maintain cell membrane integrity.

The main fatty acids in the omega-3 group are:
- α-linolenic acid or $\omega_3\alpha$ (C18, 3 double bonds; ALA)
- eicosapentaenoic acid (C20, 5 double bonds, EPA)
- docosahexaenoic acid (C22, 6 double bonds, DHA)

The double bonds are in cis configuration, which is responsible for the helical shape of the omega-3 molecules. EPA and DHA acids can be synthesised by the human body from ALA acid, but only in small amounts.

The Italian National Hospital Cardiologists Association (ANMCO), in collaboration with the Mario Negri Institute, have conducted a study (2) which examined a sample of 11,324 patients who had suffered a myocardial infarction. After a 4-year follow-up, the patients treated with omega-3 presented a greater reduction in heart attacks, sudden death, strokes and total mortality than those who received no treatment. Taking one gram of ω-3 PUFA a day for 3.5 years significantly improved the prognosis of patients who suffered heart attacks; the benefit consists of a relative reduction of 15% in the events included in the primary end-point of total mortality, repeat heart attack and stroke. This benefit is almost entirely due to the reduction in the number of deaths (20%).

A large number of pharmaceutical formulations based on ASA have been developed since it was introduced over 100 years ago. However, the stability of ASA formulations in soft gelatin capsules has proved unsatisfactory, because acetylsalicylic acid tends to hydrolyse easily, generating salicylic acid (SA) as a degradation product. This technical problem has already been tackled in the past, as disclosed in US 20100178335, which suggested the use of cyclodextrins, especially hydroxypropyl-beta-cyclodextrin, to reduce the degradation of ASA.

However, cyclodextrins are relatively expensive, so there is still a need for stable formulations in soft capsules that use inexpensive, readily available excipients.

DISCLOSURE OF THE INVENTION

It has surprisingly been found that the use of amylose or a particular type of starch containing a high percentage of amylose improves the stability of ASA when formulated in soft capsules. The stabilisation effect is improved in the presence of an acid such as citric acid, tartaric acid or the like.

However, the stabilisation effect is absent when the common starches present on the market are used, in particular pregelatinised starch acetate and other modified starches, as the comparative example below demonstrates. The soft capsule formulation is particularly suitable for the administration of combinations of antiaggregants and omega-3 fatty acids, which are useful for the therapeutic purposes specified in the introduction.

The present invention therefore relates to formulations in soft gelatin capsules of acetylsalicylic acid (ASA), omega-3 fatty acids, an organic acid and amylose or a starch containing between 40% and 90% amylose. The preferred starches have an amylose content between 40% and 90%, preferably between 50% and 70%, and even more preferably 70%. Said starches are present in the formulations according to the invention in percentages ranging between 1% and 60%.

Amylose and high-amylose starches are generally used to give rheological characteristics to the gelatin in the soft capsule shells, to improve their chew characteristics and reduce adherence during the manufacturing and storage stages. The use of high-amylose starches as an ingredient of the gelatins employed in the pharmaceutical and nutritional sphere, in particular to make capsule shells, is known in itself. For example, U.S. Pat. No. 5,554,385 discloses the use of high-amylose starches to improve the physical characteristics of the gelatin shell. According to the invention, however, the presence of amylose or starches containing between 40% and 90% amylose in the soft capsules protects the ASA against hydrolysis to SA. This stabilisation effect can be considered wholly unexpected on the basis of the prior art.

Pharmaceutically acceptable salts of ASA include lysine, ornithine, glycine and chitosan salts, or inorganic salts of calcium, sodium, potassium and aluminium. An oily liquid or semisolid suspension of ASA (between 30 and 350 mg per pharmaceutical unit) is typically dispersed in the oily phase of the contents of the soft capsule.

The organic acid is preferably citric acid, acetic acid or tartaric acid in the mesotartaric, dextrotartaric and levotartaric forms, or other organic acids whose use is allowed in the pharmaceutical or nutritional sphere. Anhydrous citric acid in percentages ranging between 1% and 30% is preferred.

The omega-3 fatty acids present in the formulations according to the invention preferably comprise eicosapentaenoic acid (EPA) and docosahexaenoic acid (DHA) or esters thereof, such as ethyl esters, in the EPA:DHA ratio of 0.9:2.1. The unit dose of omega-3 acids or esters thereof ranges between 150 mg and 1200 mg per dosage unit.

The citric acid, amylose or starch can be contained in the gelatinous shell and/or in the inner liquid or semisolid part of the capsule.

The formulations according to the invention are stable, being characterised by a percentage of degradation products which is less than 3% by weight of the ASA after 36 months' storage at 25° C./60% RH.

The shell of the soft capsules can be prepared in the conventional way, with ingredients and excipients known to the skilled person. In particular, all the gelatins listed in the pharmacopoeia can be used as gelling agents in the soft capsule shell, such as gelatin A or B (e.g. those with a bloom strength of 80 to 300) or modified gelatin (e.g. succinylated gelatin), as can suitable substitute gelling compounds, such as those based on starch or carrageenan, certain polyphenyl compounds described in the literature, or others. Gelatin of plant or animal origin, in particular porcine, bovine, avian or fish gelatin, is preferred. The gelling ingredient is mixed with the other excipients, usually water and one or more non-volatile plasticisers, which guarantee the elasticity of the capsule. Said plasticisers are preferably polyhydroxy alcohols such as glycerin, propylene glycol, sorbitol, modified sorbitols, sorbitol/sorbitans, mannitol, macrogol 200-600 and mixtures thereof.

The water serves as a solvent and provides the mass of molten gelatin (at a temperature of around 60-70° C.) with the viscosity required for its workability. After the formation of the capsule, the water content is reduced by drying. Further excipients may be modified excipients, such as partly hydrogenated starch hydrolysates, silicone oils (such as dimethicone), or other excipients employed to formulate shells used in the pharmaceutical industry such as glyceryl behenate, beeswax, colorants, opacifiers and preservatives, and antioxidants.

As stated, the acid is not only contained in the liquid, semisolid or filling composition, but can also be contained in the shell, in percentages ranging from 0.1% to 2.5% by weight of the wet shell. The filling can contain an oily suspension of crystals, pellets, microcapsules or coated crystals.

The manufacturing method of the novel formulations according to the invention is conventional, and can be performed with all the machines available on the market for this purpose. An example of the preferred process is the "Rotary Die" process, which shapes, fills and seals the soft capsules in a single operation. In that process, two ribbons obtained from a mass of molten gelatin (or another suitable gelling compound) fill two die halves of the desired shape in the surfaces of two adjacent rotating rollers. When the die closes as a result of the rotation, the liquid or semisolid content is injected by a dispenser into the capsule thus formed, and the capsule is released when the die reopens.

The invention is described in greater detail in the examples below.

EXAMPLE 1

Preparation of a Soft Capsule Containing ASA, Omega-3, High-Amylose Starch and Citric Acid a) Preparation of Shell Ingredients, amounts for preparation, and the corresponding percentages:

| Shell ingredient | Amount (kg/batch) | % |
|---|---|---|
| Gelatin | 29.2 | 36.5 |
| Sorbitol | 14.0 | 17.5 |
| Glycerol | 4.0 | 5.0 |
| High-amylose starch (70% amylose) | 8.8 | 11.0 |
| Purified water* | 24.0 | 30.0 |

*a 5.0 kg surplus of water is also added 29.2 kg of purified water (including surplus), 14 kg of sorbitol and 4 kg of glycerol are introduced into a 150 liter turboemulsifier (OLSA-Italy). The mixture is heated to 70° C. (±5° C.) under stirring for 15 to 60 min.

When the required temperature is reached, high-amylose starch is added under constant stirring. The dispersion is mixed for 15 to 60 min under static vacuum (between −0.5 and −1 bar) at the temperature of 70° C. (±5° C.).

After mixing, the gelatin is added (300 bloom gelatin, Lapi Gelatine Italia), and the mass is maintained under constant stirring for 15 to 60 min, under static vacuum (between −0.5 and −1 bar) at the temperature of 70° C. (±5° C.).

The mass is then deaerated by applying a progressive vacuum until a value of between −0.8 and −0.9 bar is reached.

After complete deaeration, the mass is cooled to 60° C. (±5° C.) and then stored in an insulated container.

b) Preparation of Filling

Ingredients and amounts for preparation, and the corresponding percentages:

| Ingredient | Amount (kg/batch) | % |
|---|---|---|
| ASA | 1.744 | 17.44 |
| Fish oil | 4.814 | 48.14 |
| Yellow beeswax | 0.558 | 5.58 |
| Hydrogenated coconut oil | 0.221 | 2.21 |
| Refined palm oil | 0.221 | 2.21 |
| Pregelatinised starch | 1.570 | 15.70 |
| Anhydrous citric acid | 0.872 | 8.72 |

0.558 kg of beeswax, 0.221 kg of hydrogenated coconut oil and 0.221 kg of refined palm oil are mixed together in a 25 liter turboemulsifier (OLSA-Italy), and heated to 70° C. (±5° C.), applying a dynamic vacuum of between −0.9 and −1.0 bar.

When the required temperature has been reached, the fish oil is added, maintaining the mixture under stirring and dynamic vacuum of between −0.9 and −1.0 bar. After the addition, the temperature is restored to 70° C. (±5° C.), maintaining the mixture under stirring and dynamic vacuum of −0.9 to −1.0 bar.

When the target temperature has been reached, the mass is cooled to 25° C. (±5° C.), and maintained under stirring and dynamic vacuum of −0.9 to −1.0 bar.

When the temperature of 25° C. (±5° C.) has been reached, the vacuum is reduced to a value of −0.6 to −0.8 bar. At this point, 1.744 kg of powdered ASA, the pregelatinised starch and the anhydrous citric acid are added, and mixed under vacuum for between 30 and 60 min. During mixing the vacuum is restored to between −0.9 and −1.0 bar.

After mixing, the temperature must be between 23° C. and 27° C. At this point the product is discharged into a container.

c) Preparation of Capsules

Size 6 oval soft gelatin capsules were prepared according to the "Rotary Die Process". Capsules with the following characteristics were obtained:

Mean weight of capsule: 640 mg±7.5%

Mean assay: 97.1%

SA assay: 1.2%

Humidity of filling: 1.3%

Disintegration time: 6 capsules out of 6 in less than 10 min

Stability of Product described in Example 1 Expressed in Terms of % of SA after 6 Months at 25° C./60% RH and 30° C./65% RH

| Stability study conditions | Time zero | 1 month | 3 months | 6 months |
|---|---|---|---|---|
| | | SA (%) | | |
| 30° C./65% RH | 1.2 | 1.4 | 1.5 | 1.8 |
| 25° C./60% RH | 1.2 | — | 1.3 | 1.4 |

COMPARATIVE EXAMPLE 2

| Ingredients | mg/capsule | Time zero SA (%) | 1 month 30° C./65% RH SA (%) |
|---|---|---|---|
| Filling | | | |
| ASA | 75 | 2.3 | 3.3 |
| Fish oil | 207 | | |
| Yellow beeswax | 24 | | |
| Hydrogenated coconut oil | 9.5 | | |
| Refined palm oil | 9.5 | | |
| Pregelatinised starch | 67.5 | | |
| Anhydrous citric acid | 37.5 | | |
| Shell | | | |
| Gelatin | 92.95 | | |
| Sorbitol | 28.08 | | |
| Glycerol | 24.83 | | |
| Pregelatinised starch acetate | 11.83 | | |
| Purified water | 102.31 | | |

The batch produced with the formulation described in the comparative example presents at time 0 a high percentage of degradation, expressed as the % of salicylic acid, namely 2.3%.

The percentage of SA rises considerably to 3.3% after one month storage of the product at 30° C./65% RH.

EXAMPLE 3

High-Amylose Starch in Filling

| Filling ingredient | Amount (kg/batch) | % |
|---|---|---|
| ASA | 1.744 | 16.04 |
| Fish oil | 4.814 | 44.28 |
| Yellow beeswax | 0.558 | 5.13 |
| Hydrogenated coconut oil | 0.221 | 2.03 |
| Refined palm oil | 0.221 | 2.03 |
| Pregelatinised starch | 1.570 | 14.45 |
| High-amylose starch (70% amylose) | 0.872 | 8.02 |
| Anhydrous citric acid | 0.872 | 8.02 |

The composition of the shell is identical to that reported in example 1.

EXAMPLE 4

Amylose Content of Shell and Filling

| | Amount (kg/batch) | % |
|---|---|---|
| Filling ingredient | | |
| ASA | 1.744 | 16.61 |
| Fish oil | 4.814 | 45.85 |
| Yellow beeswax | 0.558 | 5.31 |
| Hydrogenated coconut oil | 0.221 | 2.10 |
| Refined palm oil | 0.221 | 2.10 |
| Pregelatinised starch | 1.57 | 14.95 |
| Amylose (100% amylose) | 0.5 | 4.76 |
| Citric acid | 0.872 | 8.30 |
| Shell ingredient | | |
| Gelatin | 29.2 | 36.5 |
| Sorbitol | 14.0 | 17.5 |
| Glycerol | 4.0 | 5.0 |
| Amylose (100% amylose) | 8.8 | 11.0 |
| Purified water | 24.0 | 30.0 |

EXAMPLE 5

Citric Acid in Shell

| Shell ingredient | Amount (kg/batch) | % |
|---|---|---|
| Gelatin | 29.2 | 36.50 |
| Sorbitol | 14.0 | 17.50 |
| Glycerol | 4.0 | 5.00 |
| High-amylose starch (50% amylose) | 8.8 | 11.00 |
| Purified water | 23.2 | 29.00 |
| Citric acid | 0.8 | 1.00 |

The composition of the filling is identical to that reported in example 1.

EXAMPLE 6

Tartaric Acid Content of Shell and Filling

| | Amount (kg/batch) | % |
|---|---|---|
| Filling ingredient | | |
| ASA | 1.744 | 16.61 |
| Fish oil | 4.814 | 45.85 |
| Yellow beeswax | 0.558 | 5.31 |
| Hydrogenated coconut oil | 0.221 | 2.10 |
| Refined palm oil | 0.221 | 2.10 |
| Pregelatinised starch | 1.57 | 14.95 |
| High-amylose starch (50% amylose) | 0.5 | 4.76 |
| Tartaric acid | 0.872 | 8.30 |
| Shell ingredient | | |
| Gelatin | 29.2 | 36.50 |
| Sorbitol | 14 | 17.50 |
| Glycerol | 4 | 5.00 |
| High-amylose starch (50% amylose) | 8.8 | 11.00 |
| Purified water | 23.2 | 29.00 |
| Tartaric acid | 0.8 | 1.00 |

EXAMPLE 7

25.0% High-Amylose Starch (70% Amylose) in Shell

| Shell ingredient | Amount (kg/batch) | % |
|---|---|---|
| Gelatin | 40.0 | 50.0 |
| Sorbitol | 8.0 | 10.0 |
| Glycerol | 4.0 | 5.0 |
| High-amylose starch (70% amylose) | 20.0 | 25.0 |
| Purified water | 8.0 | 10.0 |

The composition of the filling is identical to that reported in example 1.

EXAMPLE 8

1.0% High-Amylose Starch (70% Amylose) in Shell

| Shell ingredient | Amount (kg/batch) | % |
|---|---|---|
| Gelatin | 37.6 | 47.0 |
| Sorbitol | 13.6 | 17.0 |
| Glycerol | 4.0 | 5.0 |
| High-amylose starch (70% amylose) | 0.8 | 1.0 |
| Purified water | 24.0 | 30.0 |

The composition of the filling is identical to that reported in example 1.

COMPARATIVE STABILITY

| | Time zero | 6 months at 30° C./65% RH SA (%) |
|---|---|---|
| Example 1 | 1.2 | 1.8 |
| Example 3 | 1.1 | 1.9 |
| Example 4 | 1.3 | 1.8 |
| Example 5 | 0.9 | 1.7 |
| Example 6 | 1.2 | 1.8 |
| Example 7 | 1.1 | 1.8 |
| Example 8 | 1.0 | 1.7 |

BIBLIOGRAPHY

1. Physicians' Health Study
   Final report on the aspirin component of the ongoing Physicians' Health Study. Steering Committee of the Physicians' Health Study Research Group.
   N Engl J Med. 1989, 321(3):129-35.
2. Marchioli R, et al., on behalf of GISSI-Prevenzione investigators.
3. Early protection against sudden coronary death by n-3 polyunsaturated fatty acids after myocardial infarction: Time-course analysis of the results of Gruppo Italiano per lo Studio della Sopravvivenza nell'Infarto Miocardico (GISSI)—Prevenzione.
   Circulation 2002, 105:1897-1903.

The invention claimed is:

1. A formulation consisting of capsules consisting of shell and
   filling composition,
   said shell consisting of gelatin and amylose or a starch containing between 50% and 70% amylose;
   said filling composition consisting of acetylsalicylic acid or a pharmaceutically acceptable salt thereof, omega-3 fatty acids or esters thereof, an organic acid and amylose or a starch containing between 50% and 70% amylose.

2. The formulation according to claim 1 wherein the omega-3 fatty acids comprise eicosapentaenoic acid (EPA) and docosahexaenoic acid (DHA) or esters thereof in the EPA:DHA ratio of 0.9 to 2.1.

3. The formulation according to claim 2 wherein the EPA:DHA ratio ranges from 0.9 to 2.1.

4. The formulation according to claim 3 containing 150 mg to 1200 mg per dosage unit of omega-3 acids.

5. A formulation consisting capsules consisting of
   shell and
   filling composition,
   said shell consisting of gelatin, amylose or starch containing between 50% and 70% amylose and anhydrous citric acid in percentages ranging from 1% to 30%
   said filling consisting of acetylsalicylic acid or a pharmaceutically acceptable salt thereof, omega-3 fatty acids or esters thereof, an organic acid in percentages ranging from 1% to 30% and amylose or a starch containing between 50% and 70% amylose.

6. The formulation according to claim 1 characterized by a percentage of degradation products lower than 3% by weight after three months storage at 25° C./60% RH. 8.

7. A formulation consisting of capsules consisting of
   shell and
   filling composition,
   said shell consisting of gelatin, an organic acid and amylose or starch containing between 50% and 70% amylose;
   said filling composition consisting of acetylsalicylic acid or a pharmaceutically acceptable salt thereof, omega-3 fatty acids or esters thereof, an organic acid, amylose or a starch containing between 50% and 70% amylose, and an oil suspension of crystals and pellets.

8. A formulation consisting of capsules consisting of
   shell and
   filling composition,
   said shell consisting of gelatin, and amylose or starch containing between 50% and 70% amylose;
   said filling composition consisting of acetylsalicylic acid or a pharmaceutically acceptable salt thereof, omega-3 fatty acids or esters thereof and an organic acid.

9. A formulation consisting of capsules consisting of
   shell and
   filling composition,
   said shell consisting of gelatin, an organic acid and amylose or starch containing between 50% and 70% amylose;
   said filling composition consisting of acetylsalicylic acid or a pharmaceutically acceptable salt thereof, omega-3 fatty acids or esters thereof, an organic acid, and an oil suspension of crystals and pellets.

* * * * *